United States Patent [19]

Cipolla et al.

[11] Patent Number: 5,457,044
[45] Date of Patent: Oct. 10, 1995

[54] METHOD FOR COLLECTION OF AEROSOLIZED PROTEINS BY INERT FILTRATION

[75] Inventors: David C. Cipolla; Igor Gonda, both of San Francisco, Calif.

[73] Assignee: Genentech, Inc., South San Francisco, Calif.

[21] Appl. No.: 145,922

[22] Filed: Oct. 29, 1993

[51] Int. Cl.$^6$ .............................. C12N 9/22; C12Q 1/44; B01D 39/20
[52] U.S. Cl. .............................. 435/199; 435/19; 55/523; 95/273; 252/340
[58] Field of Search .............................. 252/340; 95/273; 55/523; 435/199, 19

[56] References Cited

U.S. PATENT DOCUMENTS

| | | | |
|---|---|---|---|
| 3,107,986 | 10/1963 | Plaut et al. | 95/273 |
| 3,744,297 | 7/1973 | Hanson et al. | 73/24.03 |
| 3,922,555 | 11/1975 | Chapuis et al. | 250/472.1 |
| 4,249,918 | 2/1981 | Argo et al. | 95/273 |
| 4,378,976 | 4/1983 | Rush | 95/29 |
| 4,883,507 | 11/1989 | Rey et al. | 95/273 |
| 5,230,884 | 7/1993 | Evans et al. | 424/45 |

FOREIGN PATENT DOCUMENTS

WO93/13752  7/1993  WIPO.

OTHER PUBLICATIONS

Niven, R. W., "Delivery of Biotherapeutics by Inhalation Aerosols", *Pharm Tech.*, 17:72–82 (1993).
Shak, S.; et al., "Recombinant human DNase I reduces the viscosity of cystic fibrosis sputum", *Proc. Nat. Acad. Sci.*, 87:9188–92 (1990).
Aitken, M. A., et al. "Recombinant human DNase Inhalation in Normal Subjects and Patients with Cystic Fibrosis: A Phase 1 Study", *JAMA*, 267:1947–1951 (1992).
Hubbard, R. C.; et al. "A preliminary study of aerosolized recombinant human deoxyribonuclease I in the treatment of cystic fibrosis", *New. Eng. J. Med.* 326:812–815 (1992).
Vogelmeier, C. et al. "Aerosolization of recombinant SLPI to augment antineutrophil elastase protection of pulmonary epithelium", *J. Appl. Physiol.*, 69:1843–1848 (1990).
Byron, P. R., "Determinants of drug and polypeptide bioavailability from aerosols deliverd to the lung", *Adv. Drug Del. Rev.* 5:107–132 (1990).
Hubbard, R. C. et al., "Fate of aerosolized recombinant DNA–produced $\alpha_1$–antitrypsin: Use of epithelial surface of the lower respiratory tract to administer proteins of therapeutic importance", *Proc. Nat. Acad. Sci.*, 86:680–684 (1989).
Oeswein, J. Q., et al. "Aerosolization of Protein Pharmaceuticals", *Proceedings of the Second Respiratory Drug Delivery Symposium*, Dalby, R. N., et al., Eds.; Continuing Pharmacy Education, Univ. of Kentucky, Ky., pp. 14–49 (1991).
Mercer, T. T., et al., "Operating Characteristics of Some Compressed–Air Nebulizers", *Am. Ind. Hyg. Assoc. J.*, 29:66–78 (1968).

(List continued on next page.)

*Primary Examiner*—Marian C. Knode
*Assistant Examiner*—Jon P. Weber
*Attorney, Agent, or Firm*—Wendy M. Lee

[57] ABSTRACT

A method for collecting an aerosolized therapeutic polypeptide of interest, such as recombinant human deoxyribonuclease I (rhDNase), is provided which enables a determination as to the effect aerosolization has on the activity and integrity of the polypeptide. An aerosol of the polypeptide is generated using a nebulizer, for example, and the polypeptide is collected in an inert filter, such as a sintered glass filter. To increase the amount of polypeptide collected, the aerosol is preferably mixed with pre-humidified dilution air at a temperature between about 40° and 55° C. The collected polypeptide is subjected to biochemical activity and integrity analysis compared to the activity and integrity of the control polypeptide which has not been aerosolized.

18 Claims, 1 Drawing Sheet

OTHER PUBLICATIONS

Colthorpe et al., "The Pharmacokinetics of Pulmonary-Delivered Insulin: A Comparison of Intratracheal and Aerosol Administration to the Rabbit", *Pharm. Res.* 9(6):764–768 (1992).

Clark, A. R. et al. "Recombinant human (rh) proteins for inhalation therapy: rhDNase aerosols—a case study", *American Assn. for Aerosol Research: 12th Annual Mtg*, Oak Brook, Ill., abst No. 10A4, (Oct. 11–15, 1993).

Cipolla, D. C. et al., "Method for recovery of nebulized proteins", J. Aerosol Medicine, abstracts of the 9th Congress, Aerosols in Medicine, Garmisch–Partenkirchen, Germany, vol. 6(Supp.), pp. 1,15 (Mar. 30–Apr. 3, 1993).

Cipolla, D. C. et al., "Method for recovery of nebulized proteins", *205th ACS National Meeting: Book of Abstracts*, abstract No. 60, (Mar. 28–Apr. 2, 1993).

METHOD FOR COLLECTION OF AEROSOLIZED PROTEINS BY INERT FILTRATION

BACKGROUND OF THE INVENTION

1. Field of the Invention

This invention relates generally to a method for collection of aerosolized proteins for biochemical analysis. In particular, the invention relates to a method for collection of aerosolized therapeutic proteins which are administered to a patient by aerosol. The collected therapeutic protein can be subjected to biochemical analysis to determine the effect that aerosolization has on the activity and integrity of the protein.

2. Description of Related Art

There has been an increase in the number of therapeutic proteins which have shown promise for administration by aerosol to the lungs of the patient for either local action or systemic absorption. For a review of these, see Niven R. W., *Pharm Tech.* 17:72-82 (1993). Recombinant human deoxyribonuclease I (rhDNase) may be administered as an aerosol to the lungs of patients suffering from cystic fibrosis. rhDNase is able to cleave DNA present in the thick, viscous secretions in the airways of the lungs of the patient thereby reducing sputum viscosity (see, e.g., Shak, S., et al., *Proc. Nat. Acad. Sci.* 87:9188-92 [1990]; Aitken, M. A., et al., *Jama* 267:1947-1951 [1992] and Hubbard, R. C., et al., *New. Eng. J. Med.* 326:812-815 [1992]). Vogelmeier, et al., *J. Appl. Physiol.* 69(5):1843-1848 (1990) and Hubbard, R. C., et al., *Pro. Nat. Acad. Sci.* 86: 680-684 (1989) discuss the neutrophil inhibitors; secretory leukoprotease inhibitor (SLPI) and alpha-1-antitrypsin, and their therapeutic potential when administered by aerosol via the respiratory route. U.S. Pat. No. 5,230,884 discloses an aerosol formulation for delivery of insulin to a patient's lungs.

It is clearly desirable to assess the effect aerosolization has on protein activity and integrity. This is especially important where the protein is to be used as a therapeutic. As discussed in Byron, P., *Advanced Drug Delivery Reviews*, 5: 107-132 (1990), aerosolization of aqueous solutions by nebulizer generates high shear forces which can denature proteins. Also, because of the surface-active nature of proteins, surface fouling and foaming of the protein can occur during nebulization of a protein solution. Oeswein et al. discuss several concerns relating to the use of aerosol generators [*Proceedings of the Second Respiratory Drug Delivery Symposium*; Dalby, R. N.; Evans, R., Eds.; Continuing Pharmacy Education, University of Kentucky: KY, pp. 14–49 (1991)]. These concerns relate to potential drug denaturation or inactivation, dose delivery efficiency and accuracy, drug stability, particle size, safety, toxicity and pharmacokinetic efficacy. A further concern with respect to non-aqueous aerosols relates to dispersibility of the protein. Oeswein et al. found that, upon aerosolization, human growth hormone (hGH) tends to form metastable, partially-unfolded intermediates which have a high tendency to aggregate. This is considered to be quite problematic, especially if aggregation results in a decrease in bioactivity, or otherwise affects immunogenicity or safety of the therapeutic protein.

There is little information in the literature concerning the effect aerosolization has on protein activity and integrity. Mercer et al. discuss capturing aerosolized small molecular weight drugs, such as sodium chloride and cesium chloride, and then drying these molecules for subsequent drug characterization (Mercer, T. T. et al., *Am. Ind. Hyg. Assoc. J.* 29: 66-78 [1968]). This procedure is not suitable for proteins which may adhere to the membrane filter collection surface and thereby denature.

Oeswein et al., supra, generated an aerosol of hGH solution using either a Turret® or an Acorn-II® nebulizer (both by Marquest) and the aerosolized protein so generated was collected by impaction on a test tube. From studies of the UV spectrum of the collected hGH it was shown that extensive non-covalent aggregation of protein had occurred (evidenced by light scattering). While Oswein and his colleagues did not discuss the percentage of hGH recovered, in the experiments disclosed herein, it was found that impaction on a test tube results in quite variable and low recovery efficiencies of the protein.

Hubbard et al. (1989), supra, studied the effect that aerosolization had on recombinant human $\alpha_1$-antitrypsin (rAAT) aerosol in vitro. An aerosol of a solution of rAAT in physiologic saline solution was generated at a rate of 10 liters/min using an Ultravent nebulizer (by Mallinckrodt). The aerosol was collected by bubbling the nebulizer output through phosphate-buffered saline (at pH 7.4) and the resultant fluid was concentrated by pressure filtration using a UM10 membrane (by Amicon). The structural and functional effects of nebulization on the protein were measured. To measure any effect nebulization had on the integrity of the rAAT, SDS-PAGE gels of rAAT before, and after, aerosolization were compared. The association rate constant ($K_a$) of rAAT for human neutrophil elastase was also measured before, and after, aerosolization to determine whether aerosolization disrupted the activity of rAAT. It was determined that aerosolization did not significantly disrupt the integrity or activity of rAAT.

Vogelmeier et al., supra used the same techniques as Hubbard et al. in order to collect aerosolized secretory leukoprotease inhibitor (SLPI), i.e. bubbling through buffer in an impinger. To assess whether aerosolization had disrupted the activity of the SLPI, the time-concentration kinetics of neutrophil elastase inhibition were measured for aerosolized and un-aerosolized SLPI. Similar techniques to Hubbard et al. were adopted in order to measure the $K_a$ of SLPI for neutrophil elastase. The integrity of rSLPI after aerosolization was also evaluated using SDS-PAGE and Western analysis. Volgelmeier et al. found that aerosolization did not appear to alter the activity or integrity of SLPI.

While Hubbard et al. and Vogelmeier et al. discuss evaluation of the integrity and activity of the collected protein, they do not discuss the percentage of protein recovered. Collecting the aerosol by bubbling through buffer in an impinger may result in low collection efficiencies because it is likely that a significant fraction of the fine aerosol droplets will remain entrained in the airstream and not be collected. Thus, it is possible that the aerosolized protein collected by these methods, although fully active and intact, is not representative of the protein that is in the fine aerosol droplets escaping collection.

Colthorpe et al., Pharm. Res. 9:764-768 (1992), discuss collection of aerosolized insulin on a multistage liquid impinger operating at 60 L/min$^{-1}$ with a reported collection efficiency of 92.5%. However, detailed analysis of protein integrity and activity was unavailable. A disadvantage associated with this method is the requirement for collection and analysis of multiple fractions to determine the effect nebulization has on protein integrity. Additionally, activity and integrity analysis of the collected protein on the terminal filter may not be possible due to surface adsorption or denaturation, drying, and difficulties encountered in resolubilizing the entrapped protein.

It is, therefore, an object of the present invention to provide a method for collection of aerosolized proteins which facilitates enhanced recovery of the aerosolized protein when compared to earlier techniques and which enables the collected protein to be evaluated to assess the effect aerosolization has on the activity and integrity of the protein.

It is a further object of the present invention to provide a method of collecting nebulized therapeutic proteins, such as rhDNase, in order to assess the activity and integrity of the therapeutic protein which would be supplied by aerosol to the lungs of a patient.

Other objects and advantages of the present invention will become apparent to one of ordinary skill in the art.

SUMMARY OF THE INVENTION

The present invention provides a method for collecting an aerosolized polypeptide of interest comprising the steps of generating an aerosol of the polypeptide and collecting the aerosolized polypeptide in an inert filter.

In another aspect, the invention provides a method for assessing the effect aerosolization has on a polypeptide of interest comprising the steps of generating an aerosol of the polypeptide, collecting the aerosolized polypeptide in an inert filter and measuring integrity or biological activity of the collected polypeptide as compared to the integrity or activity, respectively, of the polypeptide prior to aerosolization.

DETAILED DESCRIPTION OF THE PREFERRED EMBODIMENTS

DEFINITIONS

Figure 1:
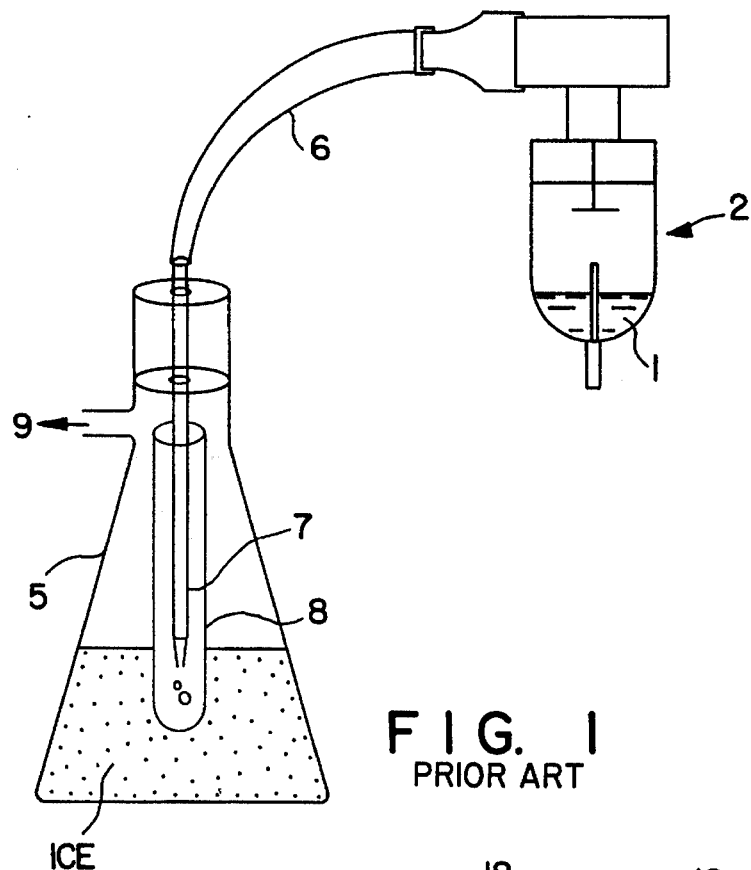
FIG. 1 depicts a schematic diagram of a test tube impaction collection apparatus illustrating earlier art used in Example 1.

As used herein, the phrase "polypeptide of interest" refers to any polypeptide for which it is desired to assess the effect aerosolization has on the activity and integrity thereof. Preferably, the protein is a therapeutic protein such as human deoxyribonuclease I (hDNase); insulin; gamma interferon; beta-1-interferon; interleukin; granulocyte colony stimulating factor; epidermal or transforming growth factors; tissue plasminogen activator; platelet derived growth factor; erythropoietin; growth hormone or Fab antibodies. Most preferred is hDNase.

The term "inert filter" is defined herein as a filter which does not substantially irreversibly adhere, or cause significant denaturation or aggregation of, or otherwise permanently alter or immobilize, the collected aerosolized protein. By "irreversible adhering" is meant binding of the protein to a filter wherein substantially all (i.e., 90–100%) of the protein retained in the filter is unable to be removed by rinsing the filter with a suitable liquid, e.g. water. According to the preferred embodiment of the invention, the filter is a coarse sintered glass filter with a nominal pore size of between about 20–80 microns, preferably between about 40–60 microns. The collection filters of the prior literature, on the other hand, tend to have pore sizes between 0.025 and 10 μm (usually between 0.2 and 0.45 μm) and are generally formed from a rigid mesh of polymeric material. Other filters such as fiberglass filters, nucleopore filters or filters coated with films preventing protein binding (e.g. siliconized materials) may also be suitable depending on the nature of the protein.

The term "integrity" relates to the primary, secondary, and tertiary structures of the native polypeptide; prior to aerosolization, wherein adverse effects on the integrity or structure of the polypeptide are indicated by, but not limited to, polypeptide oxidation, deamidation, cleavage, aggregation or denaturation caused by aerosolization.

When used herein, the phrase "biological activity" means an in vivo or in vitro effector function or activity that is directly or indirectly performed by the polypeptide. Effector functions include receptor binding, any enzyme activity or enzyme modulatory activity, any carrier binding activity, any hormonal activity, or any structural role. Where the polypeptide is an enzyme, the catalytic effector function of the enzyme may be assessed by a biological activity assay in vitro. Alternatively, where the polypeptide is a ligand, the association rate constant (Ka) of the ligand for its receptor can be assessed. Other assays for measuring biological activity of polypeptides are available to those skilled in the art.

By "enclosed housing" is meant a housing having an opening for allowing entry of the aerosol into the housing and one or more additional openings such that a vacuum can be generated within the housing.

MODES FOR CARRYING OUT THE INVENTION

The invention relates to a method for the collection of an aerosolized polypeptide of interest, preferably a polypeptide for therapeutic use. While Example 2 refers to the collection of recombinant hDNase (rhDNase) protein, this example is not intended to be limiting, and it will be readily apparent to those skilled in the art that numerous other aerosolized polypeptides can be collected for further biochemical analysis using the method disclosed herein.

According to the first step of the invention, the polypeptide of interest is aerosolized using a aerosol generator such as those well known in the art. For example, a Hudson RCI (Temecula, Calif.) T Up-Draft II, Neb-U-Mist, disposable jet nebulizer powered by a DeVilbis Pulmo-Aide compressor or the aerosol inhalation device of WO 92/20391 can be used. Other suitable aerosol generators, including compressed gas driven nebulizers, ultrasonic nebulizers, pressurized metered-dose inhalers, inhalation-driven metered dose dry-powder generators, and propellent based (non-aqueous) inhalers, may similarly be used. If a nebulizer is used, a liquid solution of the therapeutic polypeptide of interest is prepared. In this instance, the polypeptide of interest is conveniently provided in a pharmaceutically acceptable liquid carrier. An inert carrier in which the therapeutic polypeptide would normally be provided, such as water for injection, dextrose solution, saline, Ringer's solution, or a buffer such as succinate, phosphate, acetate or citrate buffer, may be utilized. If a metered dose inhaler (MDI) such as that disclosed in U.S. Pat. No. 5,230,884 is to be used, the aerosol formulation can include a propellant and a surfactant, as described in that patent, the disclosure of which is incorporated herein by reference. Suitable propellants include, e.g. chlorofluorocarbon (freon) propellants, hydrofluorcarbons (HCF's such as HFA134a and HFA227), hydrocarbons such as propane or butane, or fluorocarbons such as fluoropentane. Suitable surfactants include, e.g., glycerol phosphatide surfactants (e.g. lecithin or cephalin), polyethylene glycols and poloxamers.

In order to collect the aerosolized polypeptide of interest, an inert filter as herein defined, such as a sintered glass filter, is positioned adjacent an outlet of the aerosol generator in an operative relationship therewith so that aerosolized protein is able to be collected on the sintered glass filter. Conveniently, this can be achieved by providing the sintered glass filter in an enclosed housing as defined above, and creating a vacuum therein so as to draw the aerosol through the filter. The aerosol may, for example, be drawn through the filter at a rate of 10 to 100 L/minute, preferably 15 to 35 L/minute.

To increase the amount of aerosolized polypeptide collected, the aerosol may be drawn through the sintered glass filter together with "humidified air", which has been pre-humidified and is desirably at a temperature between about 40° C. and about 55° C., preferably at about 47° C. To pre-humidify the air, the air may be passed through a bubbler filled with water and kept at 47°±2° C. using a thermostated electrical heating device. For example, the Fisher Scientific (Pittsburg, Pa.) Isotemp Immersion Circulator, Model 730, may be used. The humidified air, when mixed with the aerosol, tends to induce condensation growth, thereby increasing the droplet size. An increase in impaction collection efficiency was found to result when humidified dilution air was supplied with the aerosol.

The aerosol generator may, for example, produce a cloud containing droplets of the polypeptide of interest at a rate of between about 5 to 80 liters per min, preferably about 5 to 10 liters per minute. The humidified dilution air may be provided at a rate of about 10 to 100 liters per minute, preferably 10 to 30 liters per minute.

The coalesced aerosol droplets in the sintered glass filter are generally drained into an ice-cooled collection flask. The polypeptide so collected can then be subjected to biochemical integrity and activity assays. The assays chosen will, of course, depend on the polypeptide which has been collected. For example, a biochemical activity assay for the collected aerosolized polypeptide which has been established in the art, can be performed. The activity of the collected aerosolized polypeptide is compared to the activity of the control polypeptide which has not been aerosolized. In the embodiment disclosed, the methyl green activity assay of Kurnick, N., *Arch. Biochem.*, 29; 41-52 (1950) was used to measure the rhDNase activity prior to, and after, aerosolization.

The integrity of the collected aerosolized polypeptide can also be compared to the integrity of a control polypeptide which has not been subjected to aerosolization. For example, the percentage of polypeptide deamidated and extent of polypeptide aggregation can be measured using techniques known in the art. By way of example, light scattering, which is indicative of the presence of high molecular weight aggregates, can be measured using a spectrophotometer.

The invention will be more fully understood by reference to the following examples. They should not, however, be construed as limiting the scope of the invention. All literature and patent citations are expressly incorporated herein by reference.

EXAMPLE 1

Collection of Aerosol using Control Test Tube Impaction Apparatus

In order to assess how effectively the control test tube impaction apparatus collects nebulized proteins, the following experiment was performed.

rhDNase was purified from cell culture supernatants and supplied in bulk solution at 4.7 mg/mL. Production of rhDNase is disclosed in Shak et al., supra. This reagent is available for clinical investigations from Genentech, Inc. This rhDNase, formulated in 150 mM NaCl, and 1 mM $CaCl_2$, pH 7.0±1.0, was diluted to 4.0 and 1.0 mg/mL with formulation vehicle (i.e. 150 mM NaCl and 1 mM $CaCl_2$, pH 7.0) for use in these experiments. With reference to FIG. 1, 2.5 mL of a 4.0 or 1.0 mg/mL rhDNase solution 1 was placed in the reservoir 2 of the Hudson RCI (Temecula, Calif.) T Up-Draft II, Neb-U-Mist, disposable jet nebulizer (Model #1734). The vacuum in the flask 5 was adjusted so that the flow rate of air through the collection device was 8.0 L/minute. This flow rate was kept steady throughout the experiment and monitored with a Sierra Instruments (Carmel Valley, Calif.) 820 Mass Flow Meter (Model #821), range 0–30 SLPM. The DeVilbiss (Somerset, PA) Pulmo-Aide Compressor (Model #5610D), with a nominal flow rate of 7 L/minute, was turned on and the nebulization was allowed to proceed for ten minutes. In all experiments, the nebulization was complete within this time as defined by a cessation of aerosol generation.

The rhDNase aerosol (generated at 7 L/minute) was diluted with 1 L/minute room air and fed into flexible tygon tubing 6 and through a narrow 2.0 mL plastic pipet 7. The larger aerosol particles exited the pipet and impacted in the ice-cooled test tube 8. The fine aerosol particles remained entrained in the air stream and were drawn away uncollected through outlet 9 by the vacuum at 8 L/minute. After the ten minute nebulization was complete, the walls of the tubing 6 and pipet 7 were rinsed and this solution was combined with the rhDNase collected in the bottom of the test tube 8. This collected rhDNase and that remaining in the nebulizer reservoir 2 were then analyzed for activity and integrity and a recovery percentage was determined as discussed below.

EXAMPLE 2

Collection of the Aerosol with the Sintered Glass Filter Collection Apparatus

Figure 2:
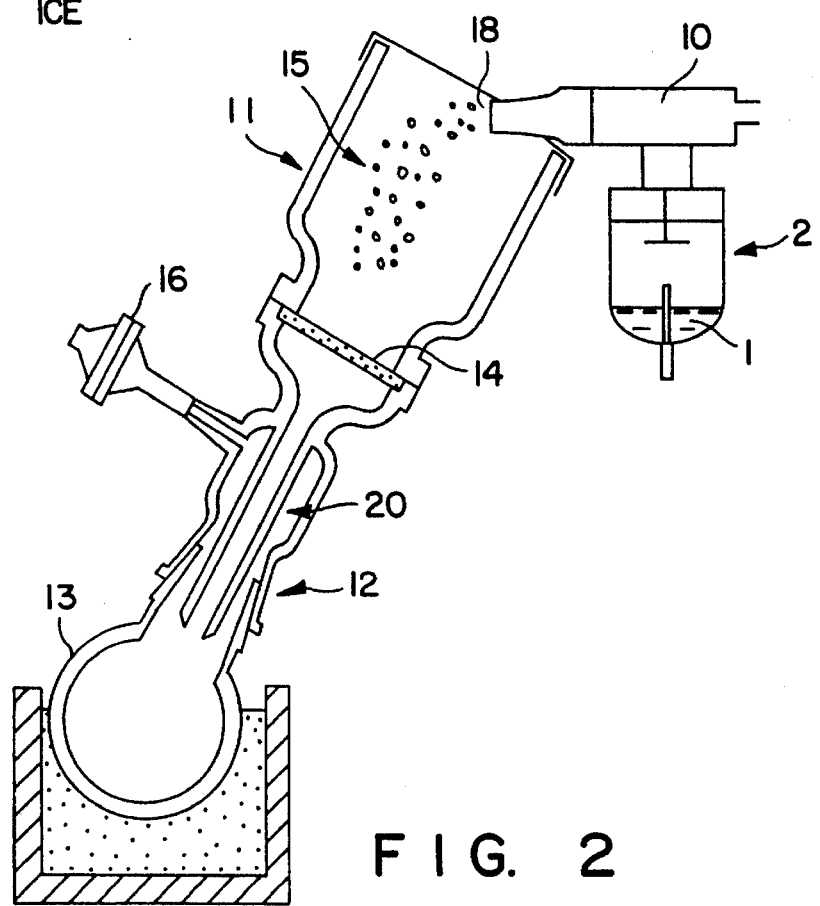
FIG. 2 depicts a schematic diagram of a sintered glass filter collection apparatus according to the preferred embodiment of the invention used in Example 2.

A nebulized rhDNase aerosol (generated at 7 L/minute as discussed in Example 1) was diluted with either room air or pre-humidified dilution air (at 16–19 L/minute). The pre-humidified dilution air was supplied through reservoir 10, shown in FIG. 2. The aerosol and dilution air were drawn at 23–26 L/minute into the pre-wetted collection housing 11 which was substantially enclosed but had an inlet 18 allowing for the entry of the aerosol into the housing 11. A vacuum was generated via the outlet 20. The humidified dilution air provided via reservoir 10 was humidified by passing it through a bubbler filled with water and kept at 47°±2° C. using a thermostated Fisher Scientific (Pittsburgh, Pa.) Isotemp Immersion Circulator, Model 730. To ensure that rhDNase was not denatured by the humidified dilution air, the temperature of the water in the bubblers was equilibrated at 47° C., well below the thermal transition temperature of about 60° C. for rhDNase. The aerosol collection housing 11 consisted of a 150 mL capacity vacuum filter funnel (coarse porosity) with a buchner joint 12 and a 50 mL round bottom flask 13 obtained from ChemGlass (Vineland, N.J.). The aerosol stream passed through the coarse sintered glass filter (40–60 micron nominal pore size) where the majority of the aerosol particles 15 impacted on, and inside, the sintered glass filter The air stream was then drawn through a 25 mm glass fiber filter 16, type A/E, Gelman Sciences, Inc. (Ann Arbor, Mich.) to determine the percent of rhDNase which escaped impaction. The liquid from the coalesced aerosol droplets in the sintered glass filter drained into the 50 mL ice-cooled collection flask 13. After the ten minute nebulization was complete, the walls of the collection housing 11 and the sintered glass filter 14 were rinsed and the liquid was drained into the collection flask 13. This collected rhDNase, and the rhDNase remaining in the nebulizer reservoir 2, were then analyzed for activity and integrity. A recovery percentage was also calculated, as discussed below.

A. Recovery Efficiencies

The recovery percentages for Examples 1 & 2 were determined. A Sartorius® (McGaw Park, Ill.) BA 4100S balance significant to 0.01 g was used to determine weights of nebulized solutions. Volumes of rhDNase were calculated from weights using a density of 1.00 g/mL. The masses of rhDNase were calculated from these volumes and from concentration determinations by UV spectroscopy.

(a) Initial rhDNase Load. A nominal 2.5 mL of either 1.0 or 4.0 mg/mL rhDNase solution was put into the nebulizer reservoir. The actual volume was determined by weighing. The initial mass load was calculated from the volume and the concentration.

(b) Percent Collected as Aerosol. The volume of the collected aerosol was determined by weighing the solution. The percent collected as aerosol is the recovered amount divided by the initial rhDNase loaded into the nebulizer ×100.

(c) Percent Remaining in the Nebulizer. The volume of rhDNase solution remaining in the nebulizer following termination of nebulization was determined by weight difference. The mass of rhDNase remaining in the nebulizer was determined by multiplying the rhDNase concentration by the volume of solution. The fraction remaining in the nebulizer is thus the recovery divided by the initial rhDNase load.

(d) Percent Recovery of rhDNase. This is the summation of the percent collected as aerosol and the percent remaining in the nebulizer. The activity and integrity of the rhDNase in these samples can be evaluated.

(e) Percent on the Filter. The dry weight of the rhDNase and salts collected on the glass fiber filter was measured with a Sartorius® (McGaw Park, Ill.) Research R200D semi-microbalance, with readability to 0.01 mg. The proportion of dry weight of rhDNase to salts in the 1.0 and 4.0 mg/mL rhDNase formulations, was calculated as follows:

| 4.0 mg/mL rhDNase Solution: | |
|---|---|
| (4.0 mg/mL rhDNase) (2.5 mL) = | 10.00 mg |
| (150 mM NaCl) (2.5 mL) (58.44 mg/mmole) (1 L/1000 mL) = | 21.92 mg |
| (1 mM CaCl2) (2.5 mL) (110.99 mg/mmole) (1 L/1000 mL) = | 0.28 mg |
| Total Dry weight = | 32.20 mg |
| Percent rhDNase by weight = 10 mg/32.2 mg = 31.1% | |

| 1.0 mg/mL rhDNase Solution: | |
|---|---|
| (1.0 mg/mL rhDNase) (2.5 mL) = | 2.50 mg |
| (150 mM NaCl) (2.5 mL) (58.44 mg/mmole) (1 L/1000 mL) = | 21.92 mg |
| (1 mM CaCl2) (2.5 mL) (110.99 mg/mmole) (1 L/1000 mL) = | 0.28 mg |
| Total Dry weight = | 24.70 mg |
| Percent rhDNase by weight = 2.5 mg/24.7 mg = 10.1% | |

From these calculations, the percent of the dry weight attributed to rhDNase was calculated. The percent on the filter was determined by dividing this number by the initial rhDNase load. This rhDNase was not assayed for activity or structural integrity; it only served to determine the quantity of rhDNase in aerosol particles that were uncollected by the sintered glass filter collection apparatus. It also allowed a determination of mass balance.

(f) Total rhDNase Recovery. This is the summation of the masses of rhDNase in the collected aerosol remaining in the nebulizer and on the glass fiber filter.

(g) Concentration Determinations using UV spectroscopy. In order to measure protein concentration, solutions of rhDNase were diluted to ≈0.5 mg/mL. The collected aerosol fractions which were less than 0.5 mg/mL were not diluted further. Each rhDNase sample was loaded into a 1 cm quartz cuvette, and the absorbance read in a Hewlett Packard (Mountain View, Calif.) 8451 Diode Array Spectrophotometer. The concentration of rhDNase was then determined using an absorptivity of 1.6 $cm^{-1}$ $(mg/mL)^{-1}$ at 280 nm without correcting for light scattering. Light scattering at 320 to 400 nm, indicative of high molecular weight aggregates, was not appreciable for any of the rhDNase solutions.

B. Protein Integrity Determination (i) Determination of protein aggregation

In order to determine whether protein aggregation had occurred during nebulization, the amount of rhDNase monomer and aggregated rhDNase in the collected samples from Examples 1 & 2 were determined using a 30 cm TSK 2000SWXL column (HP, Mountain View, Calif.). The mobile phase was 5 mM HEPES, 150 mM NaCl, 1 mM $CaCl_2$, titrated to pH 7.0 with NaOH. The flow was an isocratic 1.0 mL/minute for 15 minutes. Absorbance was monitored at 214 nm. Peak areas and retention times were recorded. The elution times of the low molecular weight Bio-Rad (Hercules, Calif.) gel filtration standards, consisting of thyroglobulin (670 kD), gamma-globulin (158 kD), ovalbumin (44 kD), myoglobin (17 kD), and cyanocobalamin (1.35 kD) allowed for the estimate of an apparent molecular size for the rhDNase species. The values for percent monomer were determined from duplicate injections.

(ii) Determination of protein deamidation

The percent of deamidated rhDNase (Asn 74 to Asp 74) was determined on an E. Merck (Gibbstown, N.J.) Separations Lichrosphere 1000 SO3 column at a flow rate of 0.5 mL/min (Cacia et al., *J. Chrom.*, 634:229-239 [1993]). Mobile phase consisted of 10 mM acetate, 1 mM $CaCl_2$, and 2 mM $MgCl_2$, pH 4.5. A linear gradient of 0 to 0.7 M NaCl was achieved in 30 minutes. Absorbance was recorded at 214 nm. Peak areas and retention times were recorded. The relative values for deamidation were determined as:

$$\left[ \frac{A_{df}/(A_{df}+A_{nf})}{A_{di}/(A_{di}+A_{ni})} - 1 \right] \times 100$$

A = area under the peak;
f = final (i.e., after nebulization);
i = initial (i.e., before nebulization);
d = deamidated rhDNase; and
n = non-deamidated rhDNase.

C. Determination of Protein Activity

To measure protein activity, the 1 mg/mL rhDNase samples were diluted sequentially into assay diluent to 0.8, 0.4, and 0.2 µg/mL and assayed in the methyl green activity assay of Kurnick, R. C., supra. Assay diluent was 25 mM HEPES, 4 mM $CaCl_2$, 4 mM $MgCl_2$, 0.1% BSA, 0.01% Thimerosol, 0.05% Polysorbate 20, pH 7.55±0.05. The active fraction of rhDNase was determined by dividing the active concentration by the concentration determined by UV spectroscopy. The active fractions were normalized by dividing by the active fraction of the 1 mg/mL rhDNase control.

RESULTS AND DISCUSSION

The recovery efficiencies calculated for Examples 1 and 2 are illustrated in Table I.

Using the sintered glass filter collection apparatus of Example 2 (see FIG. 2) with room air as the aerosol dilution air, the recovery of rhDNase increased to about 92% (a range of about 91 to 93%). In addition, 3.7±0.6% of the initial rhDNase load was collected on the glass fiber filter downstream from the collection apparatus. This was the percent of rhDNase that was present in the aerosol droplets which escaped impaction. The total recovery was thus about 96%. Therefore, about 4% of the initial rhDNase load was unaccounted for, presumably residing in collected aerosol droplets which were unrecovered in the collection apparatus. The droplets may have dried on the collection apparatus, leaving the rhDNase irreversibly bound to the collection surface.

Using preheated, humid dilution air, there was an increase in the recovery of assayable rhDNase from 92.1% to 95.8% (see Table I). The percent of rhDNase in droplets that escaped impaction decreased from 3.7±0.6% to 2.3±0.4%. Thus, summing the rhDNase in these two fractions results in an increased total recovery of rhDNase from about 96% to about 98%.

Finally, it is expected that it may be more difficult to fully recover the nebulized rhDNase during nebulizations with lower concentrations of rhDNase. This would be especially apparent if a fixed amount of protein adsorbed on the surface of the nebulizer, or was lost in a similar manner in the collection device. This lost protein would be a greater percent of the initial load for smaller initial loads of rhDNase. To test whether a significant portion of rhDNase is lost

TABLE I

| | Collection and Recovery of Nebulized rhDNase Solutions | | | | |
|---|---|---|---|---|---|
| Experiment | Percent Collected as Aerosol | Percent Remaining in Nebulizer | Percent Recovery of rhDNase | Percent on the Filter | Percent Total rhDNase Recovery |
| Example 1 [rhDNase] = 1.0 mg/mL n = 4 | 36.1 ± 5.1 | 37.0 ± 5.1 | 73.0 ± 7.1 | N.D. | N.D. |
| Example 2 [rhDNase] = 4.0 mg/mL n = 3 | 43.4 ± 1.7 | 48.7 ± 2.8 | 92.1 ± 1.3 | 3.7 ± 0.6 | 95.9 ± 1.3 |
| Example 2 with preheated humid air [rhDNase] = 4.0 mg/mL n = 5 | 45.2 ± 3.3 | 50.7 ± 3.3 | 95.8 ± 1.3 | 2.3 ± 0.4 | 98.1 ± 1.7 |
| Example 2 with preheated humid air [rhDNase] = 1.0 mg/mL n = 3 | 51.6 ± 6.6 | 43.0 ± 6.6 | 94.6 ± 0.1 | 2.0 ± 0.9 | 96.9 ± 0.9 | n = Experiment number

With reference to Table I, the mass of rhDNase from the collected aerosol and that remaining in the nebulizer reservoir was about 73% of the initial nebulizer load when the test tube impaction method of Example 1 was used (see FIG. 1). The recovery was quite variable ranging from 60 to 80%. The remaining rhDNase which was unaccounted for (about 27% of the initial load) was either in small aerosol droplets which escaped impaction, or impacted on the walls of the collection tubing and apparatus and was inefficiently recovered.

in this manner an experiment was performed with only 25% of the rhDNase used in the previous experiment by decreasing the concentration of rhDNase from 4 to 1 mg/mL. This is the concentration administered to patients in the phase 3 clinical trials of rhDNase for cystic fibrosis. There was a small, and statistically insignificant, drop in the recovery of assayable rhDNase from about 95.8% to about 94.6%. As expected, there was no change in the percent of rhDNase in droplets escaping impaction and collected in the glass fiber filter changing from 2.3% to 2.0%. The total rhDNase recovery decreased insignificantly from about 98% for 4 mg/mL rhDNase to about 97% for 1 mg/mL rhDNase.

Previous experiments suggested that nebulization alone does not alter the activity or integrity of the rhDNase solution remaining in the Hudson jet nebulizer, as rhDNase can withstand the physical rigors of repeated nebulization and impaction within the nebulizer. Thus, the presence of altered rhDNase in the collected aerosol would be likely to indicate that either rhDNase is modified during the generation and subsequent delivery of only the very fine aerosol particles which escape through the mouthpiece, or that the collection procedure itself causes rhDNase degradation. If a small, but constant, amount of rhDNase was modified during nebulization or during the collection procedure, this would be more apparent when using the lowest rhDNase concentration because the altered rhDNase would make up the largest percent of the initial load in this case. Thus, the activity and integrity of the rhDNase in the collected aerosol and that remaining in the nebulizer reservoir were analyzed only for the experiments with the 1 mg/mL rhDNase.

The absence of particulates during visual inspections and light scattering during UV spectroscopic concentration determinations suggested that neither protein precipitation nor denaturation occurred in the nebulizer reservoir residue or in the collected aerosol samples. Aggregation in the rhDNase samples was also not observed by size exclusion chromatography (i.e., SEC) as the soluble rhDNase eluted as 100% monomer (see Table II below).

TABLE II

Characterization of rhDNase Solutions

| Sample[a] | Percent Change in Deamidation | Percent Monomer | Active Fraction |
| --- | --- | --- | --- |
| Initial rhDNase Solution | 0.0 ± 1.0 | 100.0 ± 1.0 | 1.00 ± 0.10 |
| Reservoir Residual Solution | 0.0 ± 1.0 | 100.0 ± 1.0 | 0.98 ± 0.10 |
| Collected rhDNase Aerosol | 0.2 ± 1.0 | 99.3 ± 1.0 | 0.94 ± 0.10 |

[a]For all three solutions, the values for the percent change in deamidation, percent monomer, and active fraction are the average and standard deviation of three experiments using the sintered glass filter collection apparatus of Example 2 with preheated, humidified dilution air.

The area of the monomer peak correlated with the rhDNase mass load indicating no loss of rhDNase on the column. There was also no change in the percent of deamidated rhDNase, either in the nebulizer reservoir or in the collected aerosol component when compared to that of the initial sample (Table II). Finally, the methyl green activity assay indicated that the rhDNase samples were fully active within assay error when compared to the un-nebulized control rhDNase sample (Table II). Clearly, the absence of altered or inactive rhDNase suggests that rhDNase in the aerosol droplets is fully active and intact and the collection method does not alter or inactivate the rhDNase in the collected aerosol droplets.

In summary, the invention provides a method of collecting aerosolized polypeptides which has improved recovery rates compared to methods involving impaction on a test-tube and enables the collected polypeptides to be subjected to biochemical analysis to assess the effect aerosolization has on polypeptide integrity and biological activity.

We claim:

1. A method of recovering or collecting a polypeptide from an aerosol comprising contacting an aerosol containing a polypeptide with an inert filter which does not substantially irreversibly adhere, cause significant denaturation or aggregation, or otherwise permanently alter or immobilize the recovered or collected aerosolized polypeptide.

2. The method of claim 1, wherein the filter comprises a sintered glass filter.

3. The method of claim 1, wherein the polypeptide is a therapeutic protein.

4. The method of claim 3, wherein the polypeptide is human deoxyribonuclease I (hDNase).

5. The method of claim 1 wherein the polypeptide is provided in a liquid solution.

6. The method of claim 2, wherein the sintered glass filter is provided in an enclosed housing and a vacuum is generated therein so as to draw the aerosol through the filter.

7. The method of claim 6, wherein the aerosol is drawn through the filter at a rate of about 10 to 100 L/minute.

8. The method of claim 1, further comprising the step of mixing the aerosol with humidified air prior to the collection step.

9. The method of claim 8, wherein the humidified air is provided at a temperature between about 40° and 55° C.

10. A method for assessing the effect of aerosolization on a polypeptide comprising contacting an aerosol containing a polypeptide with an inert filter which does not substantially irreversibly adhere, cause significant denaturation or aggregation, or otherwise permanently alter or immobilize the recovered or collected aerosolized polypeptide, and measuring the structural integrity or biological activity of the collected polypeptide as compared to the structural integrity or biological activity respectively of the polypeptide prior to aerosolization.

11. The method of claim 10, wherein the polypeptide is a therapeutic protein.

12. The method of claim 11, wherein the polypeptide is human deoxyribonuclease I (hDNase).

13. The method of claim 10, wherein the step of measuring the structural integrity or biological activity of the polypeptide comprises measuring polypeptide aggregation or polypeptide deamidation.

14. The method of claim 1, wherein the filter has a nominal pore size of between about 20–80 microns.

15. The method of claim 2, wherein the sintered glass filter has a nominal pore size of between about 20–80 microns.

16. The method of claim 1, wherein the filter is pre-wetted prior to the collection step.

17. The method of claim 10, wherein the filter comprises a sintered glass filter.

18. The method of claim 10, further comprising the step of mixing the aerosol with humidified air prior to the collection step.

* * * * *